United States Patent
Schomburg

(10) Patent No.: US 7,022,215 B2
(45) Date of Patent: Apr. 4, 2006

(54) SYSTEM AND METHODS FOR ANALYZING COPPER CHEMISTRY

(75) Inventor: Cory Schomburg, Leander, TX (US)

(73) Assignee: Advanced Technology Materials, Inc., Danbury, CT (US)

(*) Notice: Subject to any disclaimer, the term of this patent is extended or adjusted under 35 U.S.C. 154(b) by 324 days.

(21) Appl. No.: 10/323,310

(22) Filed: Dec. 19, 2002

(65) Prior Publication Data

US 2003/0127341 A1  Jul. 10, 2003

Related U.S. Application Data

(60) Provisional application No. 60/345,977, filed on Dec. 31, 2001.

(51) Int. Cl.
  *C25D 21/12* (2006.01)
  *G01N 21/35* (2006.01)
  *G01N 27/42* (2006.01)

(52) U.S. Cl. .............. 205/81; 205/775; 205/788.5; 205/789.5; 356/300

(58) Field of Classification Search .......... 205/81, 205/82, 101, 775, 788.5, 789.5; 204/434; 356/300
See application file for complete search history.

(56) References Cited

U.S. PATENT DOCUMENTS 4,589,958 A * 5/1986 Alexander et al. ....... 205/780.5
5,192,403 A    3/1993 Chang et al.
6,280,602 B1   8/2001 Robertson
6,645,364 B1 * 11/2003 Calvert et al. ............ 205/81

OTHER PUBLICATIONS

Freeman, J.E., et al., Analytica Chimica Acta, 1985, vol. 177, pp. 121–128, especially pp. 121–122.

Cerna, N., Determination of Chlorides in an Acid Copper–plating Bath, Abstract from Povrchove Uprary, 1973, vol. 13(6), pp. 11–12.

Skoog, D.A., Principles of Instrumental Analysis, $3^{rd}$ Ed., 1985, pp. 332–337, especially p. 336.

Cheng, et al., Analysis of organic additives in Copper–plating brighteneer by High Performance Liquid Chromatography, Abstract from Sepu, 1999, vol. 17(6), pp. 602–603.

H. W. Seisler, Y. Ozaki, S. Kawata, and H.M. Heise. *Near Infrared Spectroscopy* Wiley–VCH Verlag GmbH, Weinham, Germany, 2002.

* cited by examiner

*Primary Examiner*—Roy King
*Assistant Examiner*—William T. Leader
(74) *Attorney, Agent, or Firm*—Margaret Chappius; Yongzhi Yang; Tristan Fuierer

(57) ABSTRACT

The present invention relates to methods for removing the matrix effects caused by variance in copper concentration and acidity during measurement of the organic additive concentration in a sample copper plating solution.

8 Claims, 1 Drawing Sheet

SYSTEM AND METHODS FOR ANALYZING COPPER CHEMISTRY

CROSS-REFERENCE TO RELATED APPLICATIONS

This application claims priority to U.S. Provisional Patent Application No. 60/345,977 filed on Dec. 31, 2001 and entitled "SYSTEM AND METHOD FOR ANALYZING COPPER CHEMISTRY."

BACKGROUND OF THE INVENTION

1. Field of the Invention

This invention relates to methods and apparatuses for analyzing copper plating solutions, and more specifically to methods and apparatuses for determining concentration of various components in copper plating solutions.

2. Background of the Invention

The determination of organic additives in copper plating baths is based on measuring the effect of the additives on the copper plating potential. U.S. Pat. No. 6,280,602 issued Aug. 28, 2001 for "Method and Apparatus for Determination of Additives in Metal Plating Baths" discloses the methods and apparatuses for electropotential analysis of copper plating solutions, which is incorporated herein by reference in its entirety for all purposes.

Specifically, calibration solutions are used to quantify the correlation between the electroplating potential of the copper plating solution and the additive concentrations therein. The electropotential analysis therefore relies on constant background matrix—especially copper concentration—during all phases of the determination. Some additives have a very large effect on the plating potential. In this case, only a small quantity of the sample is used for analysis, by diluting it with a standard VMS solution having known and constant copper composition. Matrix variation in such diluted sample with respect to copper concentration is negligible, because the dilution with standard VMS results in a copper concentration that is approximately the same as that of the standard VMS.

On the other hand, analysis of those additives that have less significant effect on the plating potential demands use of a much larger sample with less dilution, resulting in more matrix variation, especially with respect to copper concentration, which will inevitably affect the accuracy of the measurement results.

Therefore, an object of the present invention is to reduce the copper concentration variation in the copper plating solutions to be measured, so as to minimize the matrix effect in the organic additive concentration determination.

Moreover, changes in the acidity of the copper plating samples (due to variation in the sulfuric acid concentration therein) can cause measurement errors during the organic additive analysis, since the differences in the sulfuric acid concentration between the calibration solutions and the sample solution result in different electroplating potentials.

Therefore, it is another object of the present invention to provide a method for reducing the variation in the sulfuric acid concentrations in the calibration solutions and the sample copper plating solution to be measured.

Further, the current copper plating solution analysis techniques use ethylenediaminetetraacetic acid (EDTA) as a chelating agent for stabilizing the copper ions in the solution. However, EDTA is a well-known chelating agent that binds almost every component in the periodic table. Therefore, the use of EDTA may have adverse results, such as adsorption and clogging of the analytical tools, or none-specific binding to metal ions other than copper ions and giving false analytical signals.

It is therefore a further object of the present invention to provide a copper-specific chelating agent that does not have the above-described disadvantages of EDTA.

Other objects and advantages will be more fully apparent from the ensuing disclosure and appended claims.

SUMMARY OF THE INVENTION

The present invention in one aspect relates to a method for determining concentration of a target component in a sample copper plating solution, comprising the steps of:

(a) preparing one or more calibration copper plating solutions containing the target component of known concentrations;

(b) conducting calibration measurements on the one or more calibration solutions;

(c) conducting sample measurement on the sample copper plating solution; and (d) comparing the calibration measurement results and the sample measurement result to determine the concentration of the target component in the sample copper plating solutions, wherein the calibration copper plating solutions and the sample copper plating solution are filtered before the calibration measurements and the sample measurements, for at least partial reduction of copper ions contained therein.

Another aspect of the present invention relates to a method for determining concentration of a target component in a sample copper plating solution, comprising the steps of:

(a) preparing one or more calibration copper plating solutions containing the target component of known concentrations;

(b) conducting calibration measurements on the one or more calibration solutions;

(c) conducting sample measurement on the sample copper plating solution; and (d) comparing the calibration measurement results and the sample measurement result to determine the concentration of the target component in the sample copper plating solutions, wherein the calibration copper plating solutions and the sample copper plating solution are conditioned before the calibration measurements and the sample measurements, by adding a predetermined amount of sulfuric acid into each of such solutions.

A further aspect of the present invention relates to a method for determining concentration of a target component in a sample copper plating solution, comprising the steps of:

(a) preparing one or more calibration copper plating solutions containing such target component of known concentrations;

(b) conducting calibration measurements on the one or more calibration solutions;

(c) conducting sample measurement on the sample copper plating solution; and (d) comparing the calibration measurement results and the sample measurement result to determine the concentration of such target component in the sample copper plating solutions, wherein the calibration copper plating solutions and the sample copper plating solution are conditioned before the calibration measurements and the sample measurements, by filtering such solutions before the calibration measurements and the sample measurement for at least partial reduction of copper ions contained therein, and by adding a predetermined amount of sulfuric acid into each of such solutions.

A still further aspect of the present invention relates to a method for determining copper concentration in a sample copper plating solution, comprising the steps of adding a chelating agent comprising at least one porphyrin into said sample plating solution to form a copper-porphyrin complex with copper ions therein, and measuring concentration of said copper-porphyrin complex, so as to determine the copper concentration in said sample copper plating solution.

Yet another aspect of the present invention relates to a method for monitoring composition of at least one copper plating bath during at least one copper plating process, comprising the steps of:

(a) providing a radiation energy source that emits radiation energy having a wave-number in a range of from about 3,600 cm$^{-1}$ to about 14,000 cm$^{-1}$;

(b) directing the radiation energy emitted by such radiation energy source to at least a portion of such at least one copper plating bath;

(c) measuring absorption spectrum of the radiation energy transmitted or reflected by such portion of the at least one copper plating bath;

(d) conducting Fourier Transform-Near Infrared spectroscopic analysis on the absorption spectrum to determine the composition of said at least one copper plating bath; and (e) optionally, repeating steps (b)–(d) in sequence for multiple times throughout said at least one copper plating process, so as to monitor changes in the composition of said copper plating bath throughout the plating process.

A still further aspect of the present invention relates to an apparatus for monitoring composition of at least one copper plating bath during at least one copper plating process, comprising:

(a) a radiation energy source that emits radiation energy having a wave-number in a range of from about 3,600 cm$^{-1}$ to about 14,000 cm$^{-1}$;

(b) means for directing said radiation energy to at least a portion of said at least one copper plating bath;

(c) means for measuring absorption spectrum of said radiation energy transmitted or reflected by said portion of said at least one copper plating bath; and (d) means for conducting Fourier Transform-Near Infrared spectroscopic analysis on the absorption spectrum to determine the composition of said at least one copper plating bath.

Other objects of the present invention will be more fully apparent from the following drawings, detailed description, and appended claims.

DETAILED DESCRIPTION OF THE INVENTION AND PREFERRED EMBODIMENTS THEREOF

Figure 1:
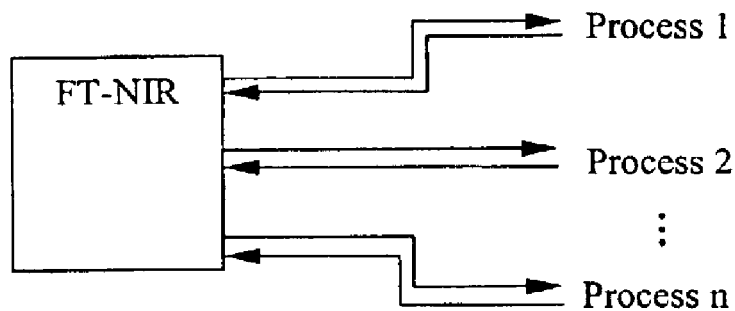
FIGS. 1–3 show three configurations of a Fourier Transfer-Near Infrared (FT-NIR) analytical cell used for monitoring the copper plating processes, according to three alternative embodiments of the present invention.

The present invention therefore standardizes measurement conditions during both the calibration measurements and the sample measurements of the copper plating solutions, with respect to the inorganic component concentrations, particularly the copper ion concentrations. In other words, the background measurements, the calibration measurements, and the sample measurements are all carried out with the same copper concentrations, which effectively eliminate the matrix effect caused by variance of the copper concentrations during such measurements.

Specifically, the present invention uses a sorbent material having affinity for copper ions to completely or at least partially remove the copper ions from both the sample and the calibration solutions, so as to reduce the variance of the copper concentration in such solutions, thereby minimizing the matrix effect caused by such variance.

Any sorbent material having sufficient absorption for copper ions (e.g. ion exchange materials) can be used for practicing the present invention. Such absorption materials are well known and readily determined by one of ordinary skill in the art.

Such sorbent material can be selected from the group consisting of polymers, aluminum phosphosilicate, ceramics, zeolites, porous silica, honeycomb matrix materials, and carbon materials. Preferably, such sorbent material is polymeric or activated carbon. One useful polymeric absorption material includes but is not limited to Dowex M4195 cation ion exchange type membrane, capable of removing at least 35 g of $Cu^{2+}$/liter resin.

In one aspect, a copper plating bath solution or calibration solution, to be measured is passed (i.e., either the sample plating solution or the calibration solution) through a pre-analysis valve, which comprises an activated carbon filter therein, to remove essentially all copper ions from such plating solution. The filtered plating solution can then be used to fill the burette for future analysis.

In another aspect of the present invention, additional sulfuric acid in an excessive amount is added to both the calibration solutions and the sample copper plating solution, which functions to normalize the acid concentration of both the calibration solutions and the sample solution and to mask any differences therebetween. In such manner, the acidity variance between the calibration solutions and the sample solution are significantly reduced, and the matrix effect caused by such acidity variance is minimized, resulting in enhanced measurement accuracy for the organic additive concentration analysis.

Specifically, a predetermined volume of sulfuric acid is added into each of the calibration solutions and the sample solution, which increases the estimated acid concentrations in any of such solutions by at least ten times (10×), preferably at least twenty times (20×), more preferably at least fifty times (50×), and most preferably at least a hundred times (100×). The term "estimated acid concentration" used herein refers to an estimation of the upper limit of the acid concentration in the copper plating solution to be measured, based on any information that is available, including actual measurement of the acid concentration in the solution.

For example, 0.1–0.5 ml of 40%–60% sulfuric acid by volume can be added to each of the calibration solutions and the sample solution. Addition of sulfuric acid of such high concentration minimizes any electropotential variances caused by different sulfuric acid concentrations in the calibration solutions and in the sample solution, and the calibration solutions and the sample solution can therefore be considered as having the same inorganic matrix, with respect to the sulfuric acid concentration, which results in less measurement errors.

Filtering of the calibration and sample solutions using sorbent and addition of excessive sulfuric acid can be carried out either separately for independent analytic cycles, or concurrently in the same analytic cycle. In a preferred embodiment of the present invention, both steps are carried out as part of the pre-measurement conditioning process for the calibration and sample solutions.

Another aspect of the present invention relates to use of porphyrins for chelating with the copper ions in the sample copper plating solution, in place of the conventionally used EDTA. Porphyrins are a group of organic chelating agents having the following ring structure:

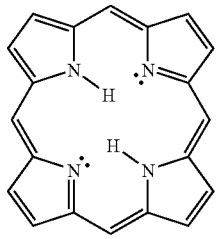

Such organic conjugated ring structure of porphyrin, if reduced to its −2 state, is capable of binding $M^{+2}$ (wherein M is a metal) ions in the center.

Specifically, the porphyrin ring is first reduced by light or a suitable reducing agent, forming the following structure:

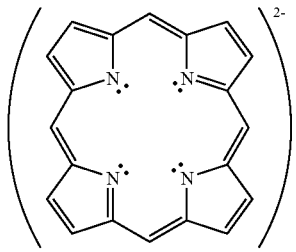

Such reduced porphyrin ring then complexes with a metal ion $M^{+2}$ (such as $Co^{+2}$, $Fe^{+2}$, and $Cu^{+2}$), to form the following porphyrin-metal complex:

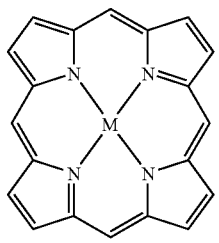

Cu-porphyrin complex demonstrates good stability, and the formation kinetics of such complex is among the highest in the +2 metal species. Therefore, porphyrin is an ideal Cu-specific chelating agent, which is less likely to bind other components in the copper plating solutions to form agglomerate or clog, in comparison with the conventionally used EDTA.

The Cu-porphyrin complex, once formed, can be easily detected and analyzed by various analytical methods, which include, but are not limited to, electrochemical analysis (such as cyclic voltammetric analysis), titration analysis, spectroscopic analysis, etc.

For example, direct electrochemical analysis may be performed on the Cu-porphyrin complex, by detecting a shift in the electrochemical properties of the $Cu^{+2}$ ions in the complexed state in comparison to that of the $Cu^{+2}$ ions in the free state. Alternatively, indirect electrochemical analysis of the Cu-porphyrin complex can be conducted by first using a titrant to react with such complex and then detecting changes of the electrochemical properties of the solution.

Specifically, cyclic voltammetric analysis can be used to analyze the Cu-porphyrin complex, on the basis that the reduction-oxidation current measured in the sample copper plating solution is proportional to the concentration of the bound $Cu^{+2}$ ions.

Titration analysis can also be performed on the Cu-porphyrin complex, if such complex is formed by using porphyrin derivatives having acid/base properties, the concentration of which can be readily determined via acid-base titrations using a pH probe.

Further, spectroscopic analysis, such as UV-Vis spectroscopic analysis, can be employed for determining the concentration of the Cu-porphyrin complexes. Porphyrins are highly colored molecules that exhibit large wavelength shifts that are specific to the types of metal ions bound to the porphyrin ring.

In one embodiment, 4,4',4'',4'''-(21H, 23H-Porphine-5,10, 15,20-tetrayl)tetrakis(benzoic acid), having a wavelength of 411 nm complexes with copper. When copper sulfate in sulfuric acid, having a wavelength of approximately 680 nm, is complexed with the porphyrin ring, the decrease in free copper ion and the increase in the porphyrin can be monitored using UV Vis spectroscopic analysis.

Therefore, the spectroscopic analysis of the Cu-porphyrin complex not only can be used for determining the concentration of $Cu^{+2}$ ions in the sample copper plating solution, but it can also be used for detecting the presence of metal contaminates in such sample plating solution.

In a still further aspect of the present invention, Fourier Transform-Near Infrared (FT-NIR) techniques are employed for monitoring the composition of a sample copper plating solution during the plating process.

Infrared analysis for copper plating solutions has low signal to noise ratio, due to the large absorption of the incident infrared light by water. FT-NIR analysis in a wave number range of from about 14,000 $cm^{-1}$ to about 3600 $cm^{-1}$ reveals the first harmonic of vibrations. The advantage of using the FT-NIR techniques instead of the FT-Infrared (FT-IR) techniques lies in that within such wave number range, the harmonics of the ionic species and the organic species in the copper plating solutions are not significantly affected by the vibrational harmonics of water. Therefore, FT-NIR analysis can be used to monitor the concentration of the ionic and organic species in sample copper plating solutions, while minimizing the impact of water absorption on the measurement results.

In a preferred embodiment of the present invention, a central FT-NIR analytical cell monitors multiple plating processes through light guiding devices such as fiber optics, which directs the near infrared light to at least a portion of each one of multiple plating baths. In such manner, multiple plating processes performed at remote locations can be monitored simultaneously, as shown in FIG. 1.

Figure 2:
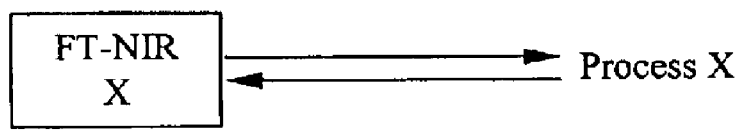

In another preferred embodiment of the present invention, each plating process is monitored by at least one FT-NIR analytical cell, as shown in FIG. 2.

Figure 3:
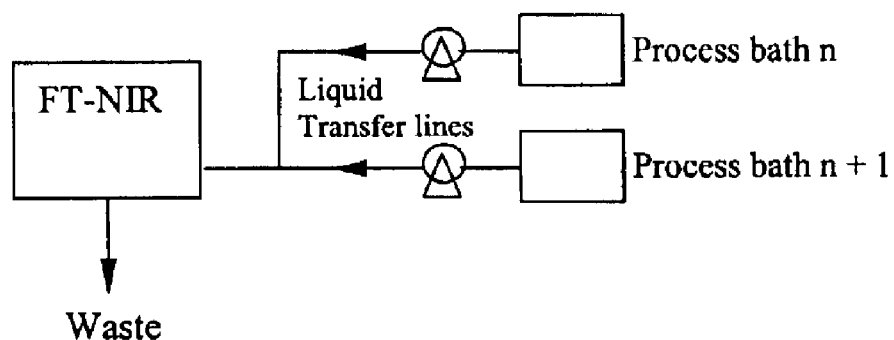

In yet another preferred embodiment of the present invention, sample plating solutions are drawn from the copper plating baths and transferred to a location in sample irradiation relationship with the near infrared light source, such as inside the FT-NIR analytical cell, via liquid transfer lines for subsequently analysis, as shown in FIG. 3.

Moreover, the sample plating solution may be vaporized for the FT-NIR analysis. It is also desirable to concentrate the sample plating solution before the FT-NIR analysis, which enhances the signal to noise ratio.

Furthermore, the FT-NIR analysis can be used in combination with electrochemical analysis, to enhance the reproducibility of the measurement results.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method for determining copper concentration in a sample copper plating solution, comprising the steps of adding a chelating agent comprising at least one porphyrin into said sample plating solution to form a copper-porphyrin complex with copper ions therein, and measuring concentration of said copper-porphyrin complex, so as to determine the copper concentration in said sample copper plating solution.

2. The method of claim 1, wherein the concentration of the copper-porphyrin complex is measured by a method selected from the group consisting of electrochemical methods, titration methods, and spectroscopic methods.

3. The method of claim 1, wherein the concentration of the copper-porphyrin complex is measured by cyclic voltammetric method.

4. The method of claim 1, wherein the concentration of the copper-porphyrin complex is measured by UV-Vis spectroscopy.

5. The method of claim 1, wherein the concentration of the copper-porphyrin complex is measured by acid-base titrations using a pH probe.

6. The method of claim 1, wherein the porphyrin comprises 4,4',4", 4"-(21H, 23H- Porphine-5,10, 15,20-tetrayl) tetrakis(benzoic acid).

7. The method of claim 1, wherein the sample copper plating solution comprises sulfuric acid.

8. The method of claim 1, further comprising the detection of metal contaminants in the sample copper plating solution.

* * * * *